(12) United States Patent
Kohn et al.

(10) Patent No.: US 8,708,495 B2
(45) Date of Patent: Apr. 29, 2014

(54) CHARACTERIZATION AND CORRECTION OF MACULAR DISTORTION

(75) Inventors: Walter Kohn, Santa Barbara, CA (US); James A. Klingshirn, Santa Barbara, CA (US)

(73) Assignee: The Regents fo the University of California, Oakland, CA (US)

( * ) Notice: Subject to any disclaimer, the term of this patent is extended or adjusted under 35 U.S.C. 154(b) by 64 days.

(21) Appl. No.: 13/112,816

(22) Filed: May 20, 2011

(65) Prior Publication Data

US 2011/0285960 A1 Nov. 24, 2011

Related U.S. Application Data

(60) Provisional application No. 61/347,445, filed on May 23, 2010.

(51) Int. Cl.
*A61B 3/00* (2006.01)
*A61B 3/02* (2006.01)
*G02C 7/00* (2006.01)

(52) U.S. Cl.
USPC .................. 351/246; 351/239; 351/159.81

(58) Field of Classification Search
USPC .................. 351/159.52, 159.78, 159.81, 239
See application file for complete search history.

(56) References Cited

U.S. PATENT DOCUMENTS

| 4,798,456 | A | 1/1989 | Enoch et al. | |
| 5,589,897 | A | 12/1996 | Sinclair et al. | |
| 5,892,570 | A | 4/1999 | Stevens | |
| 2003/0020873 | A1 | 1/2003 | Fink et al. | |
| 2007/0146631 | A1* | 6/2007 | Sinclair et al. | 351/200 |
| 2008/0309878 | A1* | 12/2008 | Hirji | 351/223 |
| 2008/0309879 | A1* | 12/2008 | Hirji | 351/223 |

FOREIGN PATENT DOCUMENTS

GB 2457735 A * 8/2009

OTHER PUBLICATIONS

International Search Report mailed Aug. 25, 2011, International application No. PCT/US2011/037404, International filing date May 20, 2011.

* cited by examiner

*Primary Examiner* — Jordan Schwartz
(74) *Attorney, Agent, or Firm* — Gates & Cooper LLP

(57) ABSTRACT

A method and apparatus for correcting vision in macular degeneration patients. Following a diagnostic procedure which has been successfully tested to determine the factors needed to correct the vision of a patient with macular degeneration, the present invention describes a prototype correcting procedure and device using a computer program and display device. Through manipulation of a grid and quantitative analysis of the manipulations, the extent and correction factors needed to correct the vision of a macular degeneration patient are discussed.

9 Claims, 18 Drawing Sheets

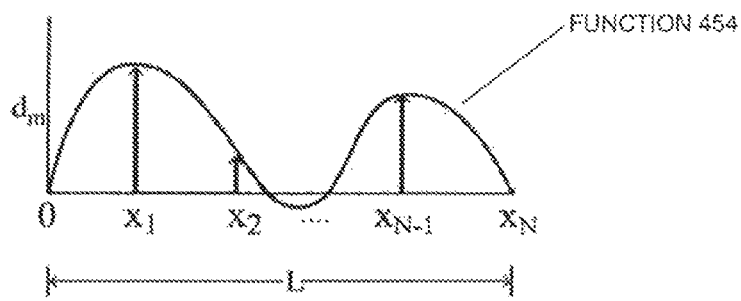

$d(x_m)$ = displacement of $\overline{x_m}$ due to MD determined in the diagnostic test.

The expression of $d(x_m)$ as a fourier series is:

$$d(x_m) = \sum_{\alpha=1}^{N} A^\alpha \sin\left(\frac{\pi \alpha x_m}{L}\right)$$

Where:

$$A^\alpha = N^{-1} \sum_{m=1}^{N} d(x_m)\left(\sin\frac{\pi \alpha x_m}{L}\right)$$

This allows interpolation of $d(x)$ for arbitrary values of x.

$$d(x) = \sum_{\alpha=1}^{N} A^\alpha \sin\left(\frac{\pi \alpha x_m}{L}\right)$$

Generalized in two dimensions to:

$$d(x_m, y_n) = \sum_{\alpha=1}^{N} A^{\alpha\beta} \sin\left(\frac{\pi \alpha x_m}{L}\right) \sin\left(\frac{\pi \beta y_n}{L}\right)$$

Where:

$$A^{\alpha\beta} = N^{-2} \sum_{m=1}^{N} \sum_{n=1}^{N} d(x_m, y_n) \sin\left(\frac{\pi \alpha x_m}{L}\right) \sin\left(\frac{\pi \beta y_n}{L}\right)$$

FIG. 4C

Perceived by Technician

Perceived by Patient

Before MD and before correction

Perceived by Technician

Perceived by Patient perceived only by Patient

With added MD and before correction perceived only by Technician

With Added Correction

CHARACTERIZATION AND CORRECTION OF MACULAR DISTORTION

CROSS-REFERENCE TO RELATED APPLICATIONS

This application claims the benefit under 35 U.S.C. Section 119(e) of U.S. Provisional Patent Application Ser. No. 61/347,445, filed on May 23, 2010, by Walter Kohn and James Klingshirn entitled "OPTICAL CORRECTION TECHNIQUES FOR MACULAR DEGENERATION", which application is incorporated by reference herein.

BACKGROUND OF THE INVENTION

1. Field of the Invention

The invention relates to macular degeneration of the eye, and specifically to optical correction techniques that will assist people with macular degeneration to see more clearly.

2. Description of the Related Art

FIG. 1 illustrates a cutaway view of the eye.

Eye 100 is illustrated, with various parts of the eye 100 shown. Those parts that are most familiar to people are the iris 102, pupil 104, lens 106, cornea 108, and retina 110. The iris 102, the "colored" portion of the eye 100, contracts and expands within an opening of the sclera 112 (the "white" part of the eye 100) to change the size of pupil 104, such that light entering the eye 100 through the cornea 108 and lens 106 passes through the vitreous portion 114 and strikes the retina 110. The choroid 116, which lies between the retina 110 and sclera 112, provides the vascular layer and connective tissue between the retina 110 and sclera 112, and as the retina 110 is stimulated by incoming light transmits information from retina 110 to the brain.

The part of the retina 110 that is responsible for central, i.e. "sharp" vision is the macula 120. The macula is a small, oval shaped spot on the back of the retina 110, and is typically about 2.5 to 3 mm in diameter. Near its center is the fovea (not shown), which contains a high concentration of cone cells. Cone cells in the macula 120 detect light and retransmit it as nerve impulses to the brain via the optic nerve 118. The cone cells in the portion of the retina 110 surrounding the fovea and macula 120 are less dense, and are responsible for the so-called peripheral, blurred vision of eye 100.

The health of the eye 100 depends on many factors, and various conditions affect different portions of the eye 100 described above. One condition which is becoming more common is age-related macular degeneration (MD), which is a chronic eye condition that typically affects people age 50 and older, and is the leading cause of severe vision loss in those over 60.

MD affects the macula 120, which is critical for acute vision, reading, and recognizing faces. MD can occur in people of any age, but usually affects older people. Because of lengthening average life-expectancy, MD has become increasingly common, and thus, the study and treatment of MD has become increasingly more important.

In a person with MD, the macula 120 begins to deteriorate in various ways. In particular, distorted central vision occurs in or near the center of the visual field. MD is associated with photoreceptor damage and a roughened macula 120, often caused by the presence of fluid or blood in the subretinal space. This roughening results in distortion of the patient's central field of vision. There are two types of MD, "dry MD" and "wet MD." Symptoms usually develop gradually and painlessly, and vary depending on the form. Most cases of MD start as the dry type, which also is the most common type. In 15 percent of cases, the disease advances to the wet type, often causing rapid vision loss.

The current approach to treatment of both types of MD vary depending on the patient and the type of MD. Treatments typically include injectable drug therapy, photodynamic therapy, laser treatment, surgery, and vitamin and mineral supplements to slow the advance of the disease. Research is focused on slowing or stopping the progression of the disease.

Thus there is a need in the art for devices that can improve the vision of MD patients. It can also be seen, then, that there is a need in the art for methods, apparatuses, and devices to help those with MD regardless of the current state of a given patient's vision.

SUMMARY OF THE INVENTION

To overcome the limitations in the prior art described above, and to overcome other limitations that will become apparent upon reading and understanding the present specification, the present invention discloses various techniques and devices to correct or partially correct the vision of a MD patient.

A method for quantitatively and non-invasively characterizing a patient's MD is disclosed and the results are used to provide a cost effective corrective device for the patient. The corrective device can be a computer screen, a camera and a mobile computer, a pair of appropriate MD eyeglasses or contact lenses, or a custom made glass slab which incorporate the correction factors.

BRIEF DESCRIPTION OF THE DRAWINGS

Referring now to the drawings in which like reference numbers represent corresponding parts throughout:

FIG. 4C illustrates an arbitrary function illustrated in one dimension analyzed with an embodiment of an interpolation function of the present invention;

DETAILED DESCRIPTION OF THE INVENTION

In the following description of the preferred embodiment, reference is made to the accompanying drawings which form a part hereof, and in which is shown by way of illustration a specific embodiment in which the invention may be practiced. It is to be understood that other embodiments may be utilized and structural changes may be made without departing from the scope of the present invention.

Overview

The present invention describes methods and apparatuses for quantitatively characterizing the distorted vision of a MD patient, and for providing methods and apparatuses for quantitatively correcting that distorted vision.

Amsler Grid

Figure 1:
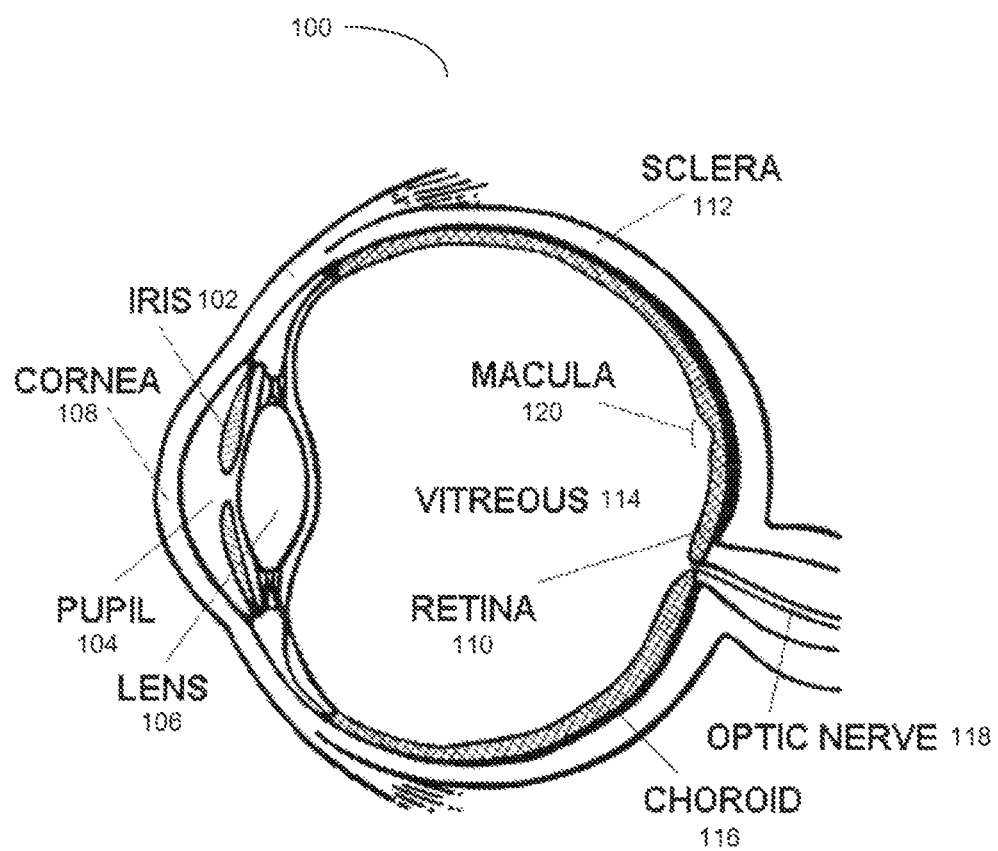
FIG. 1 is a cutaway view of the eye.
Figure 2:
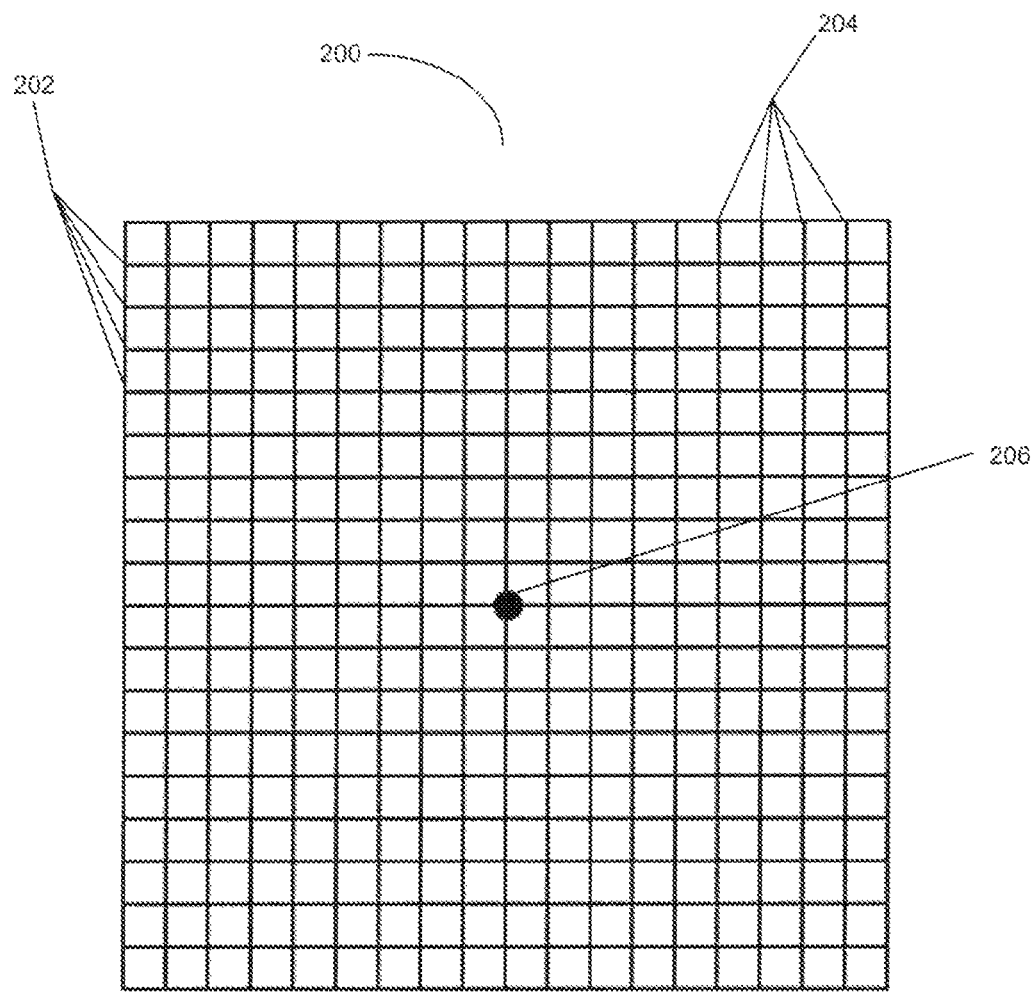
FIG. 2 illustrates an Amsler Grid.

FIG. 2 shows an Amsler Grid.

Amsler Grid 200 is a square grid of horizontal lines 202 and vertical lines 204, with a central spot 206, that has been used to characterize the health of a person's central visual field. Typically, the grid 200 is used merely to detect and monitor distortions in the visual field and how these distortions may change over time. Amsler Grid 200 is typically a square grid, typically 10 cm×10 cm divided into 20×20=400 squares.

When viewed by a person with healthy central vision, the grid appears to be "undistorted," e.g., each area defined by horizontal lines 202 and vertical lines 204 appears to be the same, with angles at 90 degrees throughout grid 200, and no dark spots or changes in contrast are registered by the viewer.

Figure 3:
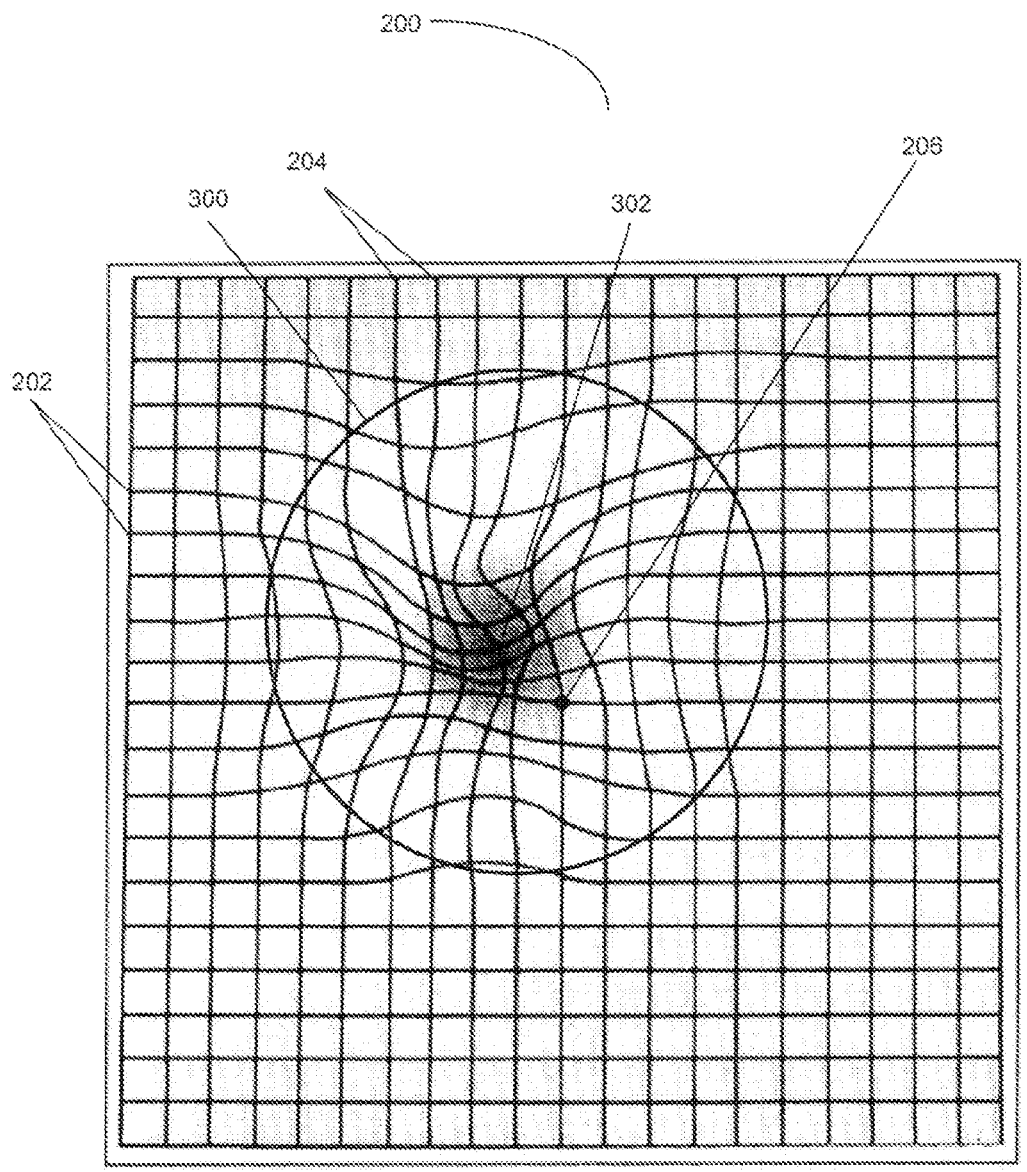
FIG. 3 illustrates an Amsler Grid as seen by a patient with macular degeneration.

FIG. 3 illustrates an Amsler Grid as seen by a patient with MD.

When a patient with MD views grid 200, one or more of the horizontal lines 202 and/or vertical lines 204 appear "distorted," e.g., that the horizontal line 202 or vertical line 204 does not appear straight, does not appear to cross other lines at 90 degrees, and the area defined by lines 202 and 204, is not uniform throughout the grid. As such, area 300, defined by the circle on grid 200, will look distorted to a given patient. Area 300 can take any shape, and can appear anywhere on grid 200; each patient will perceive the grid differently and record those perceptions differently.

Since a healthy macula 120 is typically very flat and smooth, any distortions in area 300 and dark spot(s) 302 are called "roughening" of the macula 120 surface, e.g., due to bursting of small blood vessels or new blood vessels growing underneath the macula.

To date, the Amsler Grid 200 has been used primarily as a non-quantitative tool to characterize vision. The patient is asked to view the grid, and to describe any perceived distortions. For example, the patient might have been asked if the grid is more distorted than it appeared at the previous check-up. The present invention uses a specialized Amsler Grid as a quantitative tool which is essential for the creation of a correcting device.

Figure 9A:
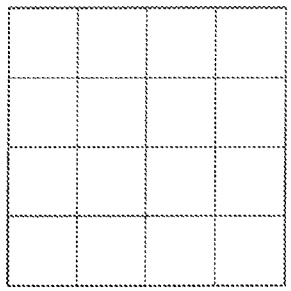
FIGS. 9A-9F illustrate a timeline of perceptions by a patient and a technician in accordance with one or more embodiments of the present invention.
Figure 9B:
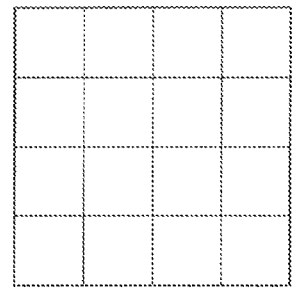
Figure 9D:
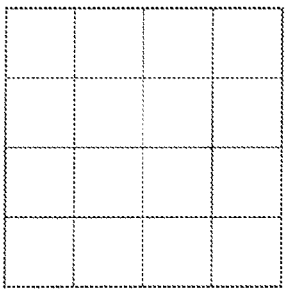
Figure 9C:
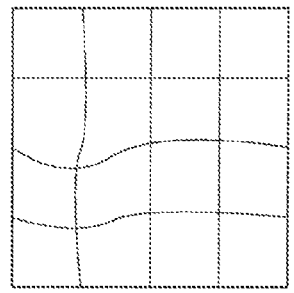
Figure 9F:
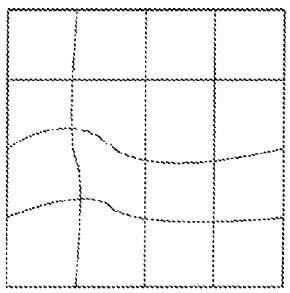
Figure 9E:
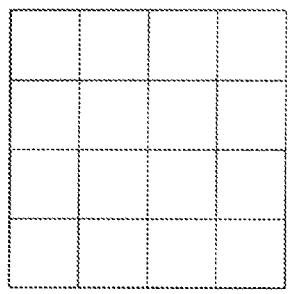

To clarify the general principles which apply to all implementations, we begin with a scenario in which a new patient whose macular degeneration has been quantitatively diagnosed, as previously discussed, is seated nest to a technician. They are both in front of a monitor which shows an Amsler grid and textual or other visual material. Before the patient developed macular degeneration they both would have seen all the presented material clearly and correctly, see FIGS. 9A and 9B. With the patient's added MD and before correction, he sees this material distorted, see FIG. 9C, while, of course, the technician's vision remains unaffected, see FIG. 9D. When one of the possible corrections is applied to the presented material, the latter is distorted in a compensatory way so that the patients perception is back to normal as shown in FIG. 9E while the technician sees the presented material as distorted by the action of the device as shown in FIG. 9F. Finally, the patient, with now normal vision can walk away with the device, as can the technician without the device.

Quantitative Assessment and Feedback

Figure 4A:
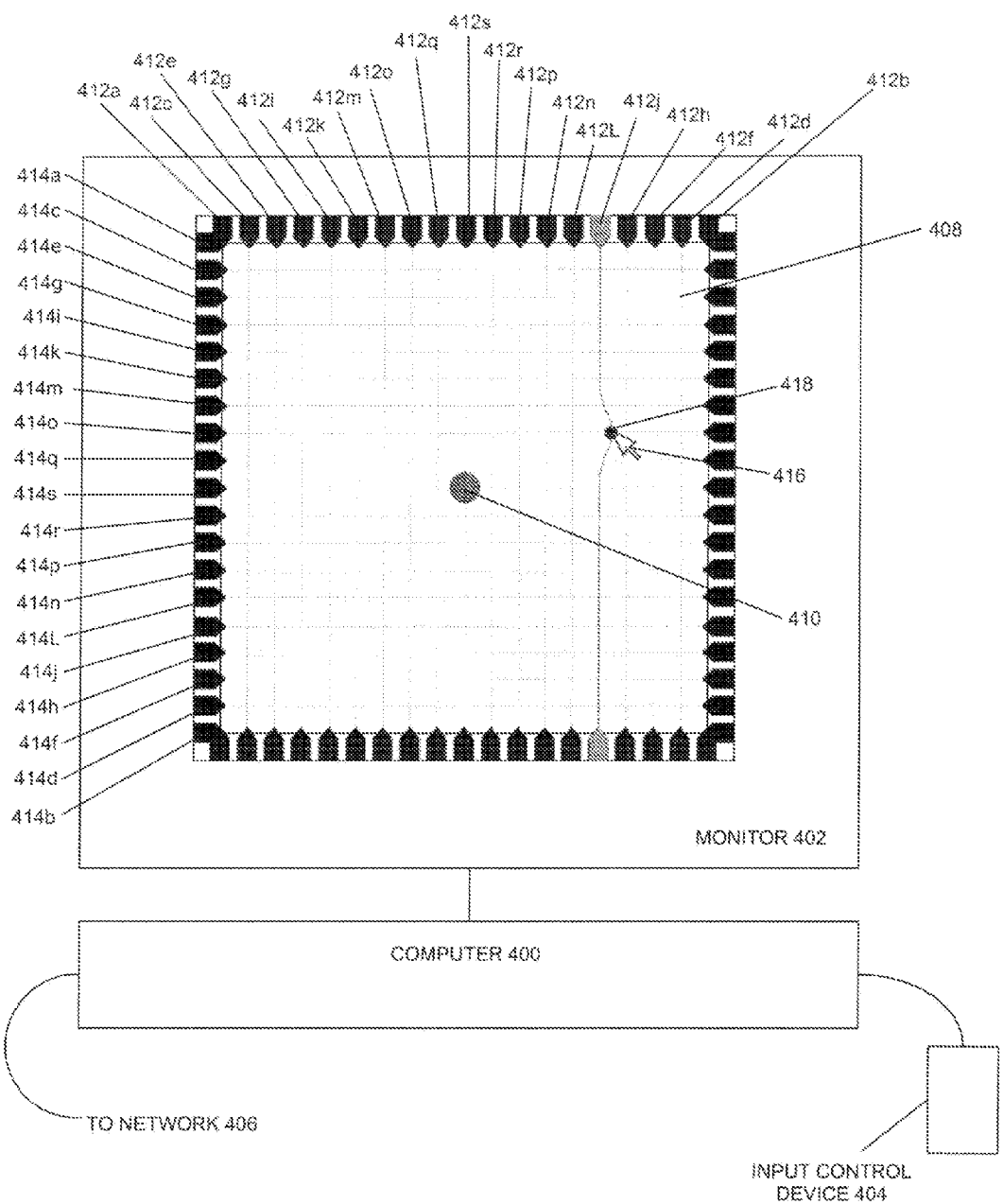
FIG. 4A illustrates an Amsler Grid used for quantitative assessment and feedback from the patient in accordance with one or more embodiments of the present invention.

FIG. 4A illustrates an Amsler Grid used for quantitative assessment and feedback in accordance with one or more embodiments of the present invention.

Computer 400, with monitor 402 and input control device 404, are shown. Computer 400 can be any type of computing device, e.g., a Personal Computer (PC), Macintosh (Mac) computer, or a touch-screen device such as an iPad or touch-screen netbook, without departing from the scope of the present invention. Further, computer 400 can be coupled to a network 406, either via wires or a wireless connection, to allow for additional processing on the inputs and outputs or delivery of new inputs and/or outputs if desired. Such computing platforms are well known in the art, and the specifics of each of the computers 400 are contemplated within the scope of the present invention, e.g., if the computer 400 is a touch screen, then input device 404 would be the screen of monitor 402 rather than a separate keyboard, mouse, or other device, etc.

As shown in FIG. 4A, a specialized Amsler Grid 408 is shown on monitor 402. Specialized Amsler Grid 408 is programmed into computer 400, or is accessible to computer 400 via network 406. Specialized Amsler Grid 408 has a central point 410, a plurality of horizontal lines 412a-410s and a plurality of vertical lines 414a-414s, similar to the Amsler Grid 200 shown in FIG. 2. However, Specialized Amsler Grid 408 of the present invention allows a user (patient) to move the horizontal lines 412a-412s and vertical lines 414a-414s in a particular way to quantify the distortion seen by the user (patient).

The present invention allows the patient to move each line, e.g., horizontal line 412j which can be highlighted for the patient's ease of detection, in specific ways to transform the "distorted" grid that the patient sees into a "normal" grid such as would be perceived by a patient without MD.

Diagnostic Test—Grid Transformation

Using input control device 404, the present invention allows the patient to move the intersection points of the horizontal lines 412a-412s and 414a-414s of specialized Amsler Grid 408 in such a way that, when completed, the edited grid looks to the patient like a perfect Amsler grid.

Initially, specialized Amsler Grid 408 is set up such that it looks to the technician like a "normal" Amsler Grid (e.g. Amsler Grid 200). The patient, usually seated with a technician, focuses his vision and attention on center spot 410, and moves the intersections of the lines 412-414 until the modified specialized Amsler Grid 408 appears to the patient to be a "normal" Amsler Grid.

In one embodiment of the present invention, the patient is seated next to a technician and viewing the same monitor 404. The patient's chin is placed at a fixed distance from monitor 404, typically in a chin rest, to keep the patient's eyes at a fixed viewing distance from monitor 404.

The monitor displays a specialized Amsler grid 408. The ratio of the Amsler grid 408 width and height to the viewing distance is typically 1:4, but can have other values without departing from the scope of the present invention. For example, and not by way of limitation, if the Amsler grid 408 displayed on the monitor is 10×10 cm, then the viewing distance would typically be 40 cm.

Detailed Technical Description

The procedure of the present invention is typically repeated twice, once for each eye, but can be repeated as many times as desired or only performed once if desired. The eye that is not being tested is typically covered or otherwise blocked.

At the beginning of the diagnostic procedure, the patient perceives the grid as distorted, while the technician perceives it as undistorted. During the diagnostic procedure, the patient uses the computer mouse to move the intersection points of the Amsler Grid 408 in such a way that when completed, he perceives the edited Amsler Grid 408 as undistorted.

During the editing procedure the computer 400 records the displacement vectors $D_{mn}$, of all intersection points of the Amsler Grid 408. These displacements are stored in the computer 400 as a set of displacement vectors:

$$D_{mn} = \{u(x_{mn}, y_{mn}), v(x_{mn}, y_{mn})\}.$$

$$m, n = -10 \text{ to } 0 \text{ to } +10 \text{ (or } 0\text{-}20)$$

These displacements constitute the diagnosis of the patient's spatial MD distortions.

During the editing procedure, the computer 400 presents the specialized Amsler Grid 408 with most of the lines 412-414 in a lighter shade, e.g., grey, and either automatically highlights one of the lines, e.g., line 412j as shown in FIG. 4A, or allows the patient to manually select any of the lines 412-414 to edit.

Once a grid line 412-414 is selected, e.g., grid line 412j, the endpoints of the selected line 412j and/or line 412j itself is highlighted, e.g., the color of the line 412j is changed to a different color than the remainder of the lines in grid 408, or the contrast of line 412j is changed with respect to the remainder of the lines in grid 408, such that it is easy for the patient to detect the selected line 412j.

The patient then places a cursor 416 on the selected line 412j, which is constrained by computer to "snap" to the intersection points between the selected line 412j and the other lines (in this case, lines 414a-414s) in grid 408. The intersection point that is selected by the placement of cursor 416, which is being controlled by input control device 404, is also typically "highlighted" for the user to make it easier for the user to determine when selected line 412j has been moved to the proper correction point. Again, this is shown by point 418, which can be shown in a different color or other visual indicator to show the patient which point 418 of the selected line 412j is being moved with input control device 404.

The highlighted intersection point can be manually moved by the patient, by dragging it with input control device 404 until it is in the correct position, or the highlighted intersection point can be automatically moved by the computer, while the patient uses input control device 404 to indicate whether the new position is better or worse than the previous position. The order in which the grid lines are selected, and the order in which the line intersection points are selected can be manually chosen by the patient, or the computer can automatically guide the patient through a preset ordering of lines and intersection points. So for example, and not by way of limitation, the computer 400 can start the patient on line 412a, and move the point 418 from the intersection of lines 412a and 414a to the intersection of lines 412a and 414b upon an input from the patient, can allow the patient to randomly select which line 412-414 to start with and where to place point 418, or any combination thereof.

To the technician, prior to the start of the manipulation of grid 408, grid 408 will appear undistorted, while, to the patient, the grid will appear distorted. While fixing the gaze on the center point 410, which also may be highlighted or otherwise rendered on monitor 404 to assist the patient in maintaining focus at this point 410, the patient either systematically, randomly, or with assistance from the computer, edits one grid line 412a-412s and 414a-414s at a time.

The endpoints of each line are typically maintained at a fixed position on the grid 408, whereas the intersection points of grid lines 412a-412s and 414a-414s are manipulated by the patient. The endpoints of grid lines 412a-412s and 414a-414s can be maintained at fixed positions with respect to Amsler Grid 200 because the periphery of the grid 408 is close to the boundary between central and peripheral vision, and is known to be very weakly distorted in an AMD patient. Therefore visual cues for keeping the eye centered, and for helping to straighten the interior of the grid typically reside at the periphery and at the center of grid 408. Since peripheral vision is typically not color sensitive and has low resolution, peripheral cues, such as the endpoints of grid lines 412a-412s and 414a-414s, and center point 410, are typically to be large with high contrast.

Grid Editing Procedure

Typically, the patient works from the outside into the center, editing one grid line 412a-412s and 414a-414s at a time. The selected grid line 412a-412s and 414a-414s is highlighted, while all other grid lines 412a-412s and 414a-414s are dimmed.

After a grid line 412a-412s or 414a-414s has been selected, the patient uses the input control device 404, e.g., computer mouse, touch screen, and/or arrow keys to move the intersection points 418 of the grid 408. A grid intersection is typically selected by clicking on the point 418 with a mouse; when selected, it is highlighted, dragged with the mouse, and clicked again to fix the point, or some other indication is made by the patient that the dot is in a "correct" position as viewed by the patient.

Internally the computer 400 uses a coordinate system that makes grid 408 look horizontal and vertical to the technician. When the patient edits a vertical line 412a-412s, the grid 408 intersection of the selected line 412a-412s is constrained by the computer 400 so that the intersection can only be moved to the left and right in the computer's coordinate system. Because of his macular degeneration the patient will in general perceive this movement as not exactly vertical.

In the first phase, the patient will straighten out all of the vertical lines 412a-412s as well as can be performed given time and peripheral vision of the patient. When this phase is completed, all of the vertical lines 412a-412s will look perfectly straight to the patient and pass through the appropriate boundary points at the periphery of grid 408. In the second phase, without regard to the vertical lines, the patient similarly straightens out all horizontal lines 414a-414s. Computer 400, similarly, constrains movement of the intersections of horizontal lines 414a-414s to move only up and down in the computer's coordinate system. However, because of the macular degeneration, this second phase alignment by the patient slightly disturbs the alignment of the vertical lines. Therefore the entire process may need to be iterated one or more times.

The distortion seen by the patient at the beginning of the procedure, and the distortion seen by the technician at the end of the procedure are called complementary. The distortion seen by the technician at the end will have the same magnitude but will have the opposite sign, e.g., movement seen by the patient in a positive x-direction will be seen by the technician as a movement in the negative x-direction.

Two Dimensional Discretized Displacement Vectors

The coordinates of the undistorted Amsler grid intersections are denoted by $$r_{mn} = (x_{m,n}, y_{m,n}) \qquad m, n = 0, 1, 2 \ldots N \qquad N = 20$$

The 21×21 displacement vectors defined at all the points on the Amsler grid 408, which are necessary to remove the distortions of the grid 408 perceived by the patient, are denoted as $$d_{mn} = (u_{mn}, v_{mn})$$

These displacement vectors represent the quantitative diagnosis of the geometry of each patient's macular degeneration.

$u_{mn}$, $v_{mn}$ Displacement Vector Components

All grid coordinates are defined in cartesian coordinates from the perspective of a normal viewer. Since the edges of the Amsler Grid 408 are constrained as fixed with respect to a "normal" Amsler Grid 200, these components vanish on the edges of the Amsler grid 408.

The intersection points of the distorted grid are denoted by $r'_{mn}$. They are characterized by the original grid coordinate positions plus the displacement vectors:

$$r'_{mn} = r_{mn} + d_{mn}$$

Figure 5:
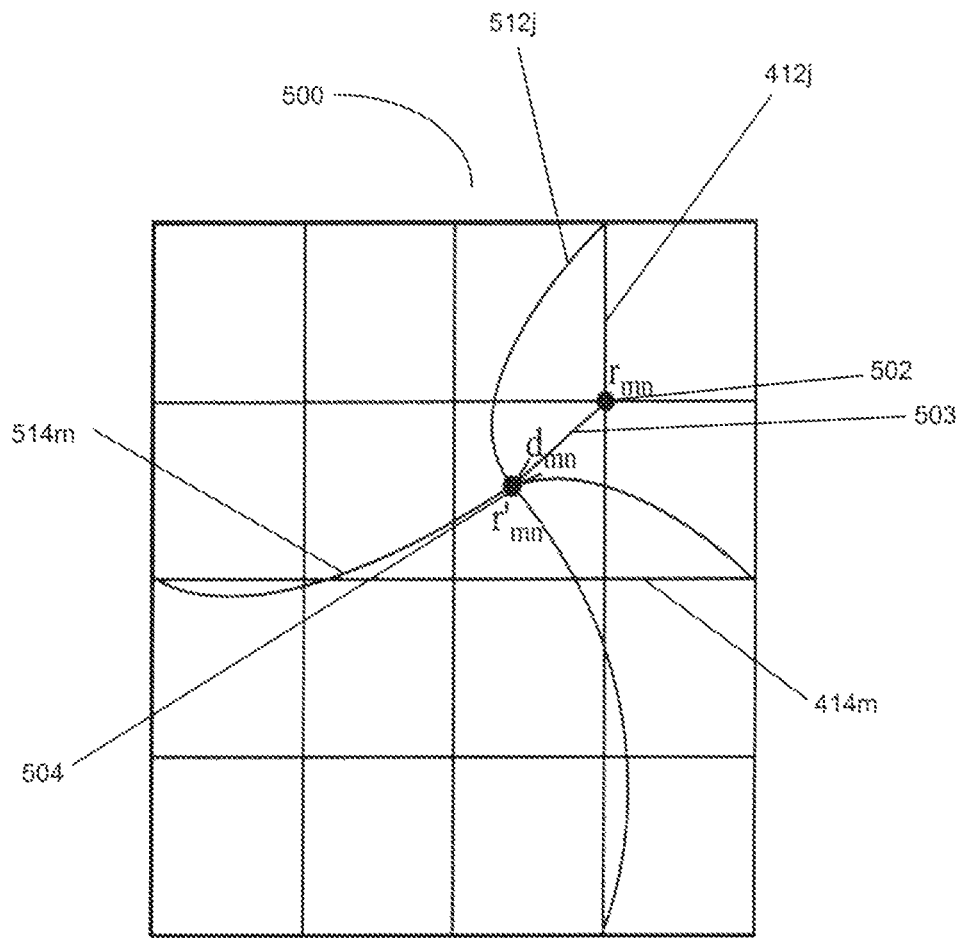
FIG. 5 illustrates the definition of the displacement vector $d_{mn}$ shown with a coordinate system defined in the perspective of a person with normal vision. The vector $d_{mn}$ is formed by displacing a grid intersection point from its initial postion $r_{mn}$ to its final postion $r'_{mn}$.

The movement of individual grid 408 intersections and the use in determining the correction factors are discussed with respect to FIG. 5.

The two dimensional set of vectors associated with the $N^2$ displacement intersections constitute the patient's diagnosis $d_{mn}$. The displacement vectors $d_{nm}$ are used to compute the distorted image that looks to the patient like a perfect image. A high resolution version of the a digital distortion field, when applied to the page of a book, will be easier for the patient to read, as discussed with respect to FIG. 4B.

Displacement Vector Field Interpolation

The displacement vector field that is defined by the quantitative diagnosis has about 400 vectors with the resolution of 20×20 cells within the Amsler grid 408. For practical applications, higher resolution may be required. A typical digital image has a resolution of several million pixels. For example, a moderately priced digital camera has resolution of 3648× 2736 pixels, for a total resolution of approximately 10 million pixels. A two-dimensional interpolation scheme is used to increase the resolution of the displacement vector field from the original 20×20 resolution, to a resolution that matches the image that is being distorted. The patient obviously cannot move 10 million individual pixels into new positions, and thus interpolation must be employed.

Sine Transform for Two-Dimensional Interpolation

The two-dimensional displacement vectors associated with the $N^2$ intersections of the Amsler Grid 408 express the diagnosis, and the present invention utilizes an interpolation schema to increase the resolution of the diagnosis. Although described with respect to a particular interpolation method herein, other methods of interpolation are possible within the scope of the present invention.

FIG. 4C illustrates an arbitrary function illustrated in one dimension analyzed with an embodiment of an interpolation function of the present invention.

Function 454, also referred to as arbitrary function $d_m$, is drawn as a function of variable x. The values of $d_m$ at each grid 408 position $x_m$ are known, and are designated $d(x_m)$. The interpolation functions create a function that passes exactly through each point $d(x_m)$ and provides an expression $d(x)$ for arbitrary values of x.

Equation 455 which is the expression for $d(x_m)$, is a summation of N sine functions with successively decreasing wavelength. The first term in the series, $\sin(1\pi/L)$ has a half wavelength of L, where L is the length of the side of the grid 408. The second term has a full wavelength across the grid 408 width, etc., and the final component has a component $\sin(20\pi/L)$ which has a half wavelength within a single square in grid 408.

The $A^\alpha$ terms are the amplitudes of the individual sine functions for each of the sine components within the series. Equation 456 which is the Fourier inversion of equation 455 gives an expression for finding the $A^\alpha$ terms. Equation 457, the interpolation function, uses the $A^\alpha$ amplitudes to provide an expression $d(x)$ for arbitrary values of x.

The straightforward generalization of the above one dimensional equations into two dimensions results in equations 458 and 459. Equation 458 gives a function that can be evaluated to find the displacement value $d(x,y)$ for arbitrary values of x and y. Equation 459 is the inverse Fourier transformation of equation 458, which provides the amplitude coefficients $A^{\alpha\beta}$.

Thus, the resolution of grid 408 defines the minimum size of a visual defect that the present invention can correct; for example, and not by way of limitation, if the grid 408 square is 0.5 cm on a side, then the highest resolution sine function will have a wavelength of 0.5 cm. However, by using different grid 408 sizes, or, for example, having the grid 408 have a smaller resolution in specific areas, smaller defects can be corrected for using the present invention. So, for example, grid 408 can have smaller grid sizes in the center (where the center of the visual field has a much higher resolution and therefore needs more exact correction), and larger squares at the periphery of grid 408.

Displacement of Amsler Grid Lines

FIG. 5 illustrates a displacement of specialized Amsler Grid lines in accordance with one or more embodiments of the present invention.

Grid 500 shows a "normal" Amsler grid with lines 412j and 414m that are unmodified and viewed as linear and perpendicular by computer 400 and a healthy eye, and lines 512j and 512m after being edited by a patient with AMD to correct for his perceived distortion.

Figure 6A:
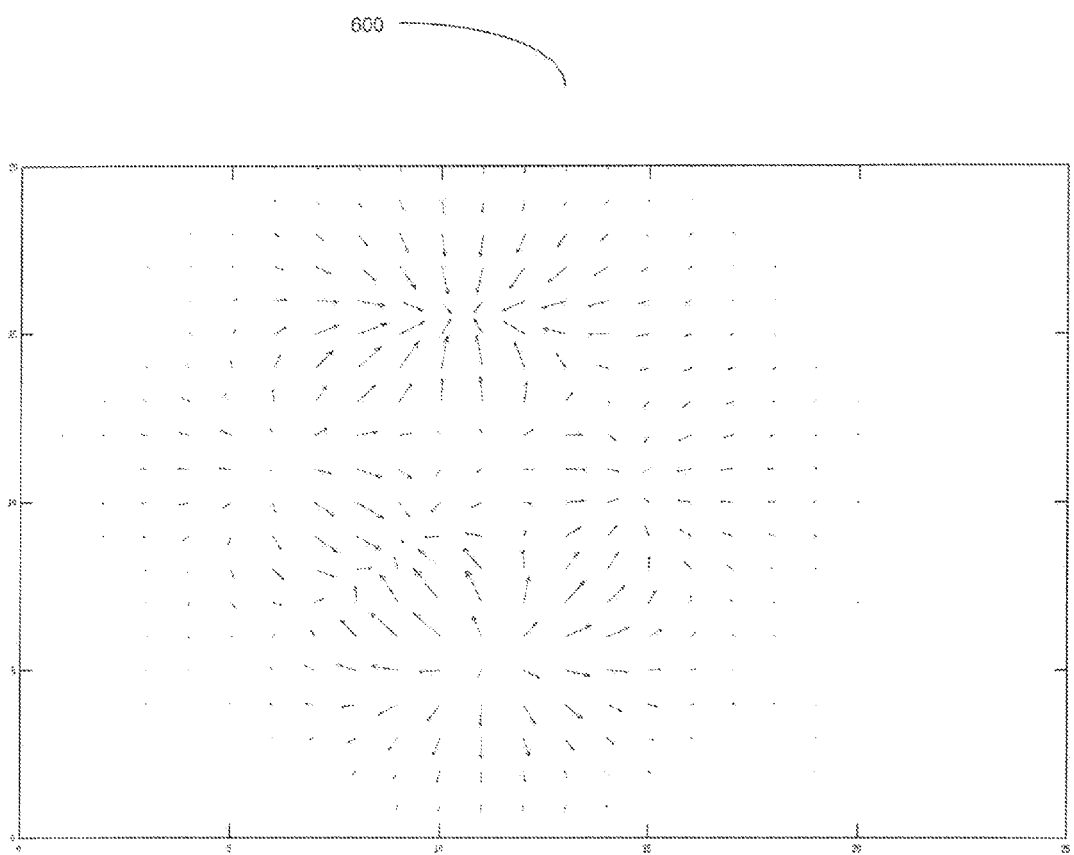
FIGS. 6A-6B illustrates an arbitrary vector field remapping having both gradient and curl components, and an interpolation of this field to a larger array, in accordance with one or more embodiments of the present invention.
Figure 6B:
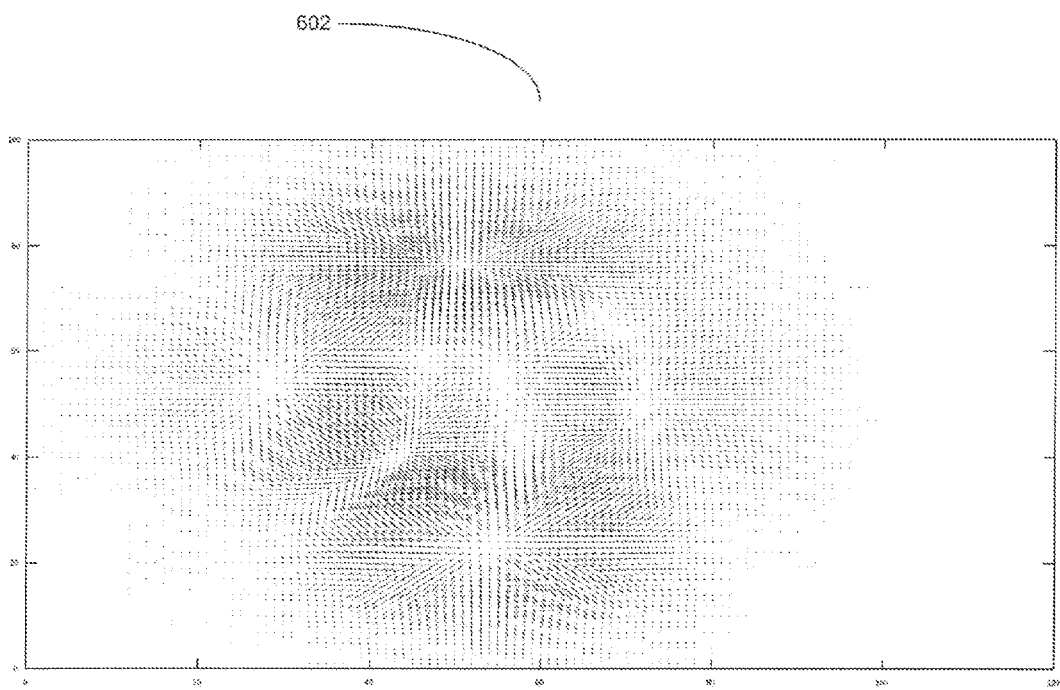

In the standard coordinate system, point 502 is where lines 412j and 414m intersect. However, as described herein, the patient has moved these intersection points, and, in the example shown in FIG. 5, has moved this to point 502. Computer 400 can now compute the magnitude change in both horizontal and vertical directions for point 502 now moved to point 504, as well as for all other intersection points for each of the lines 412 and 414 (now moved to lines 512 and 514) in grid 408. By remapping the grid 408 into this new coordinate space, monitor 402 now has correction factors based on the displacement vectors 503 to apply to a given image displayed on the monitor 402 to allow the image to appear "normal" to the patient (and to be distorted to a viewer with healthy vision). FIG. 6A illustrates an example vector field 600, showing such a mapping of grid 408, and FIG. 6B illustrates a 100×100 interpolated displacement vector field 602 generated by interpolating the diagnostic results shown in FIG. 6A.

Computer Corrective Optics

Figure 4B:
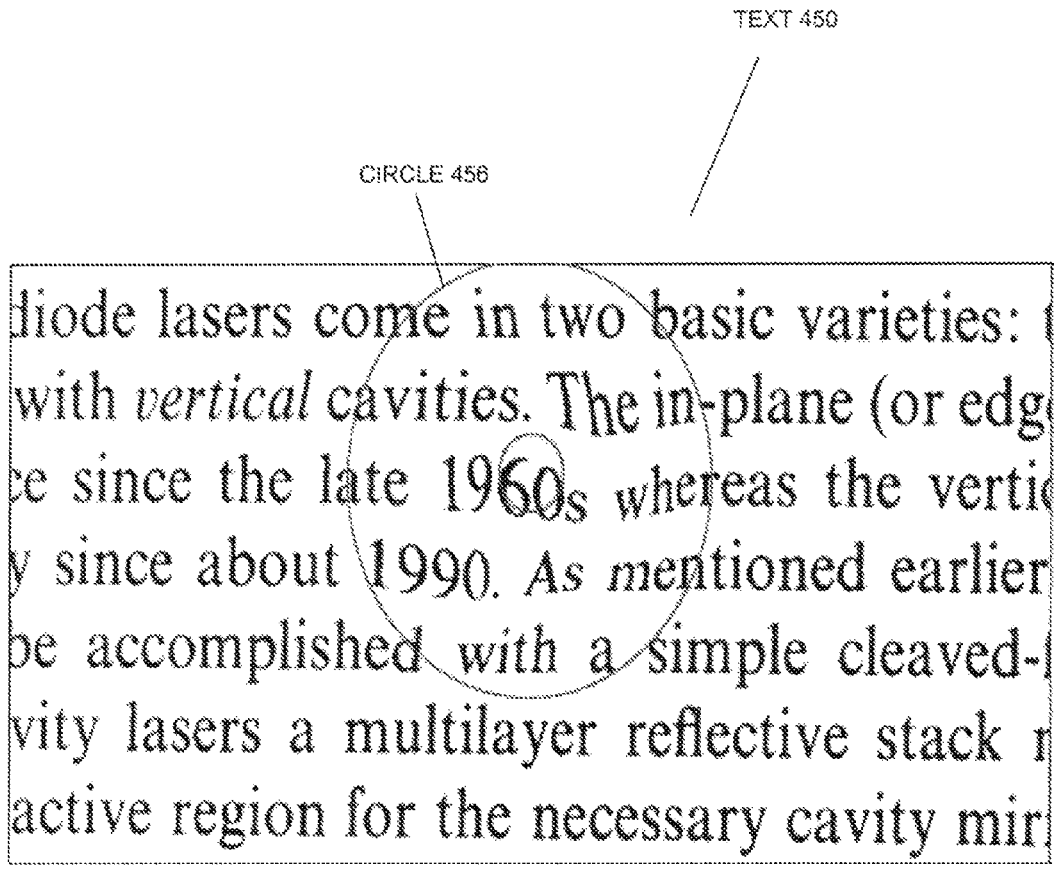
FIG. 4B shows an example of undistorted reading material being displayed on a computer screen as seen by an MD patient.

The present invention corrects the distorted vision caused by MD by applying a compensating distortion to the material displayed on a computer screen. FIG. 4B shows an example of undistorted reading material (text 450) being displayed on a computer screen as seen by the MD patient. The distortions perceived within the circle 456 by the MD patient can be corrected by applying the compensating distortion which improves the patient's reading ability.

Normally as a person reads, his eye scans the page from left to right. For the MD patient, the compensatory distortion needs to be centered at the center of the patient's field of view. This implies that the compensating distortion should move from left to right as the eye scans from left to right. The present invention has a mode where the distortion field repeatedly sweeps across the reading material following the text, from left to right, starting at the top of the page, and moving downward, at a speed controlled by the patient. The patient keeps his eyes fixed on the center of the distortion field as it sweeps, aided for example by a cross-hair indicator.

Another embodiment of the present invention keeps the distortion field centered on the reading material. The reading material is streamed through the distortion field at a speed controlled by the patient.

Each of the patient's eyes will require its own compensating distortion field. The patient might cover one eye, and read with the better eye. Alternatively, a stereo vision approach could be employed.

After completion of the diagnostic procedure, and with the aid of interpolation, the perceived spatial distortions can be corrected by application of compensating distortions. When the patient views an object using the compensation method, his perceived macular distortions will be eliminated (or at least substantially corrected).

Compensating for Distortion by Computer

Figure 6C:
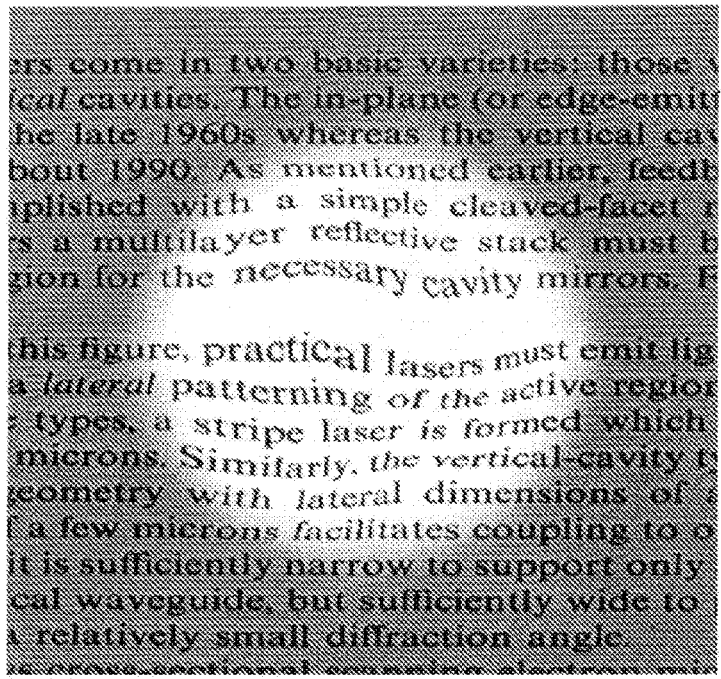
FIGS. 6C and 6D illustrate a computer-based compensation method in accordance with one or more embodiments of the present invention.
Figure 6D:
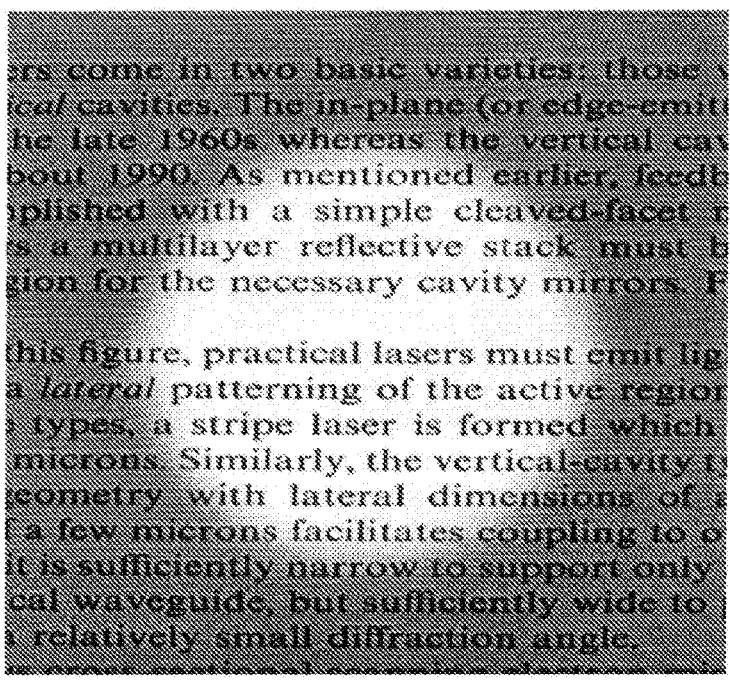

FIGS. 6C and 6D illustrate a computer-based compensation method in accordance with one or more embodiments of the present invention.

In a computer 400 based compensation method, reading material can be scanned, photographed, or otherwise converted into an array of pixels. It appears distorted to the patient, as shown in image 604 of FIG. 6C. Computer 400 software corrects the distortions by displacing each pixel using displacements obtained from the diagnostic procedure described herein. When viewed at the appropriate distance, the text now appears undistorted as shown in image 606 of FIG. 6D.

Dynamic Compensation

Figure 6E:
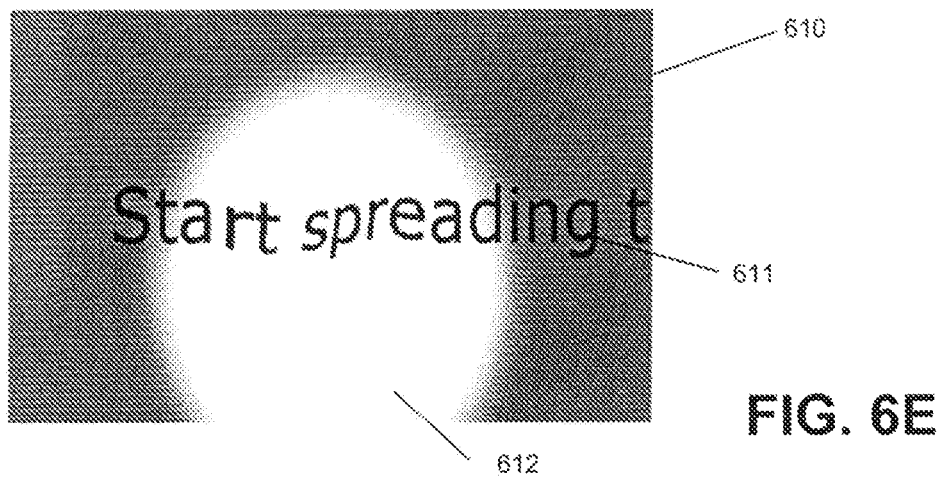
FIGS. 6E-6G illustrate a dynamic compensation scheme in accordance with one or more embodiments of the present invention.
Figure 6F:
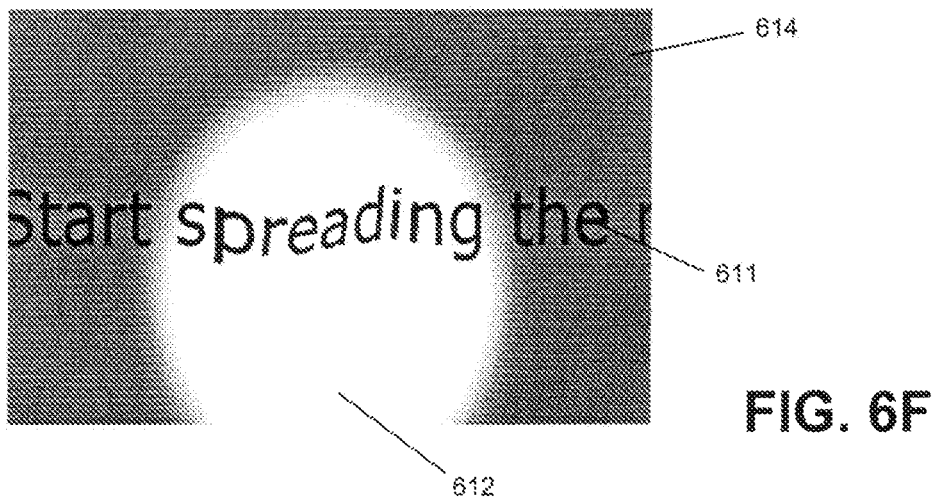
Figure 6G:
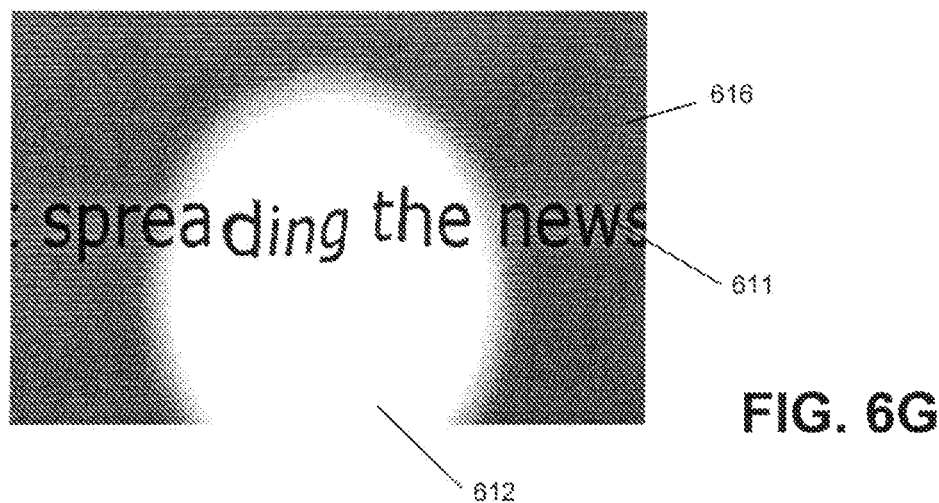

FIGS. 6E-6G illustrate a dynamic compensation scheme in accordance with one or more embodiments of the present invention.

Patients need to read entire pages, not just the small circles such as in FIG. 4b. The solution is to apply the compensation dynamically. FIG. 6E shows an example of a computer-based dynamic compensation method, where text 611 flows through the distortion field (shown highlighted as area 612) in a ticker-tape manner. The patient typically fixes his or her gaze at a fixed dot in the center of the area 612. The computer 400 then applies the compensating (anti-distortion) displacement field to the text or image within the area 612, so that it appears undistorted to the patient.

FIG. 6F shows that the text 611 has been moved to the left (the area 612 has moved to the right) in image 614. Of course, area 612 can be moved in any direction without departing from the scope of the present invention. FIG. 6G shows in image 616 that the text has moved further to the left, i.e., area 612 has moved farther to the left, to allow the patient to properly view the text in a flowing manner. Area 612 can move at varying speeds based on user inputs or automatic inputs to computer 400 without departing from the scope of the present invention.

Additional Embodiments of Computer-Based Correction Implementations

Figure 6H:
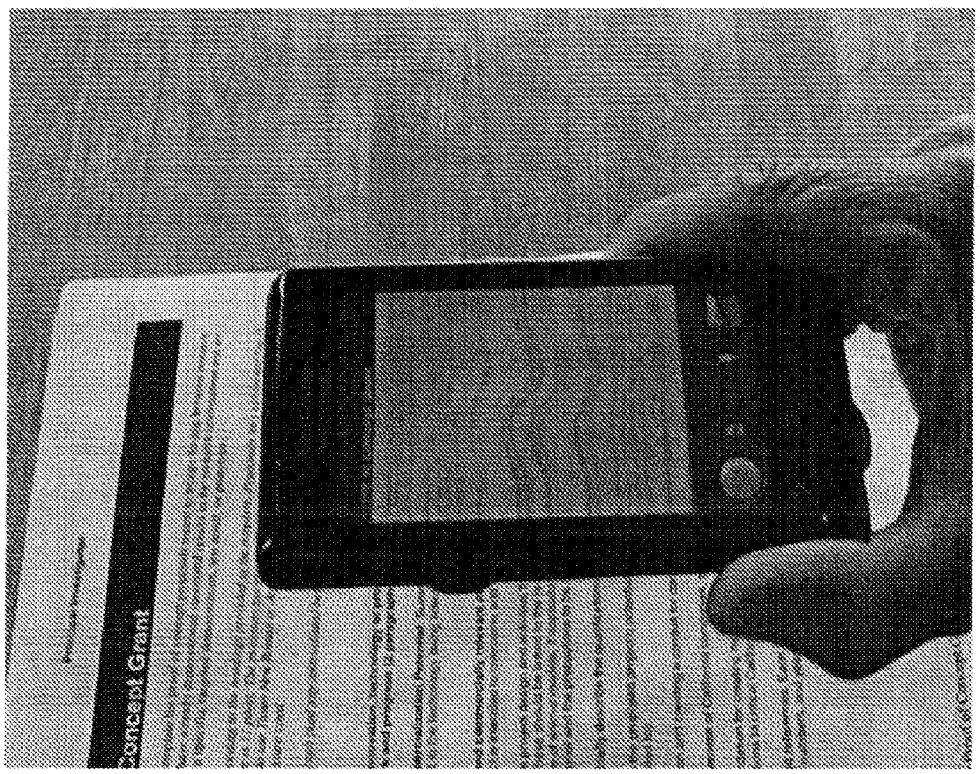
FIGS. 6H and 6I illustrate additional embodiments of computer-based compensation devices in accordance with one or more embodiments of the present invention.

FIG. 6H illustrates a handheld computer 614, e.g., cellular telephone, PDA, digital camera, etc., with a built in video camera and screen. The AMD patient scans the device 614 over the reading material. The compensating distortion is applied to the video image in real time.

Figure 6I:
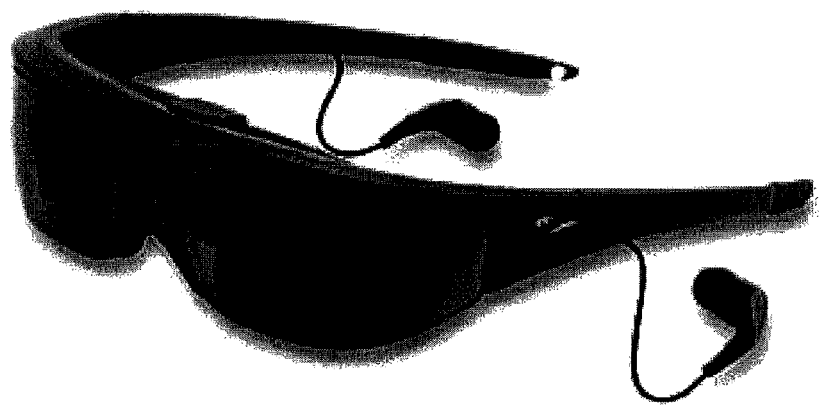

FIG. 6I illustrates existing glasses 616 for watching videos. Glasses 616 can be adapted for an AMD patient by adding a composite device comprising a small computer and video camera. The computer would apply the anti-distortion compensation to the video stream. The video glasses would then display the corrected result. A picture-in-picture technique can be employed to simultaneously display the corrected and uncorrected front view if desired.

Non-Computer Corrective Optics

Glass—Plastic—and Other Corrective Optics

It is well known that spectacles or contact lenses correct nearsightedness, farsightedness and astigmatism. The present invention employs a similar approach to solve a geometrically more challenging problem.

The present invention explains the general scheme of correcting for MD caused visual distortion, and discusses two broad approaches: One—computer based without glass or glasslike components; the other, based on refractive materials, typically glass and/or plastic, or based on deformable reflective materials, typically metal or plastic. Needless to say, these particular choices are not necessarily exhaustive.

The distorted vision created by MD is quantitatively characterized as a 2D discrete vector field $d_{mn}$. The present invention corrects the distortion caused by MD by appropriately modifying the top surface of a plate of optical glass. The modified surface causes light rays to be appropriately refracted as they travel from the reading material or other object viewed by an MD patient, through the glass, to the patient's eye. The glass is machined or otherwise processed such that the modified surface causes an apparent displacement of the reading material or other viewed object. The corrugation is typically smooth and compensates for the spatial distortion caused by the MD.

Using the results of the present invention, an arbitrary, smooth macular distortion can be corrected by a suitably patterned slab of optical material.

A refractive optical device, machined from glass or optical grade plastic, is designed using the compensating distortions on the surface of the device so that the surface contours and spatially varying thicknesses of the device cancel the distortions caused by the patient's Macular Degeneration.

Figure 10:
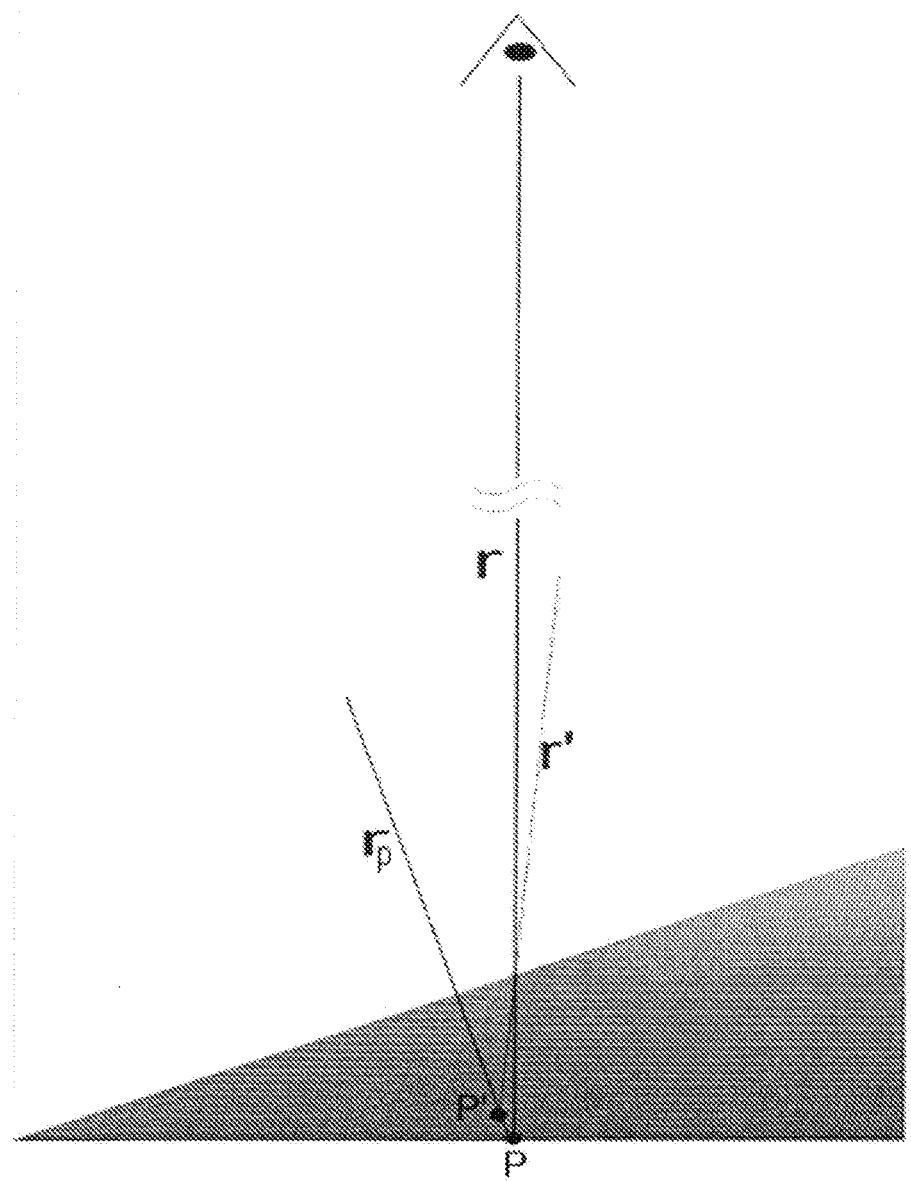
FIG. 10 illustrates the virtual displacement (lateral and/or vertical) of a luminous point on a horizontal plane by viewing it through a glass triangle.

FIG. 10 illustrates the correction of MD by Optical Refraction. A standard Amsler grid is placed on a flat surface and viewed from above. We represent the Amsler grid by a collection of closely spaced luminous points lying on the regular grid points. An MD patient will perceive the pattern of the Amsler grid points as distorted. Each point needs to be laterally moved so as to create a perfect grid. This can be accomplished by viewing the Amsler grid (one eye at a time) from a height of about 40 cm through a 10 cm by 10 cm slab of transparent material (glass, plastic) where the top surface $z=z(x,y)$ is patterned so as to eliminate the macular distortions. This is illustrated in FIG. 10, where a single luminous point P is laterally displaced to a virtual point P'. For clarity, FIG. 10 illustrates the virtual displacement of point P using a refractive triangle. This can be generalized to the geometry of an arbitrary refractive surface, by rotating and displacing the triangle in such a way that at each ray/surface intersection point, its slope matches the instantaneous slope of the arbitrary surface. In FIG. 10, a light ray, r is drawn from the luminous point P to the eye. The ray is bent by refraction at the surface of the triangle, creating ray r'. A second ray $r_p$ from luminous point P, perpendicular to the triangle surface is chosen. The virtual point P' exists at the intersection point of r' and $r_p$.

Another method of using a refracting optical device for correcting macular distortion would take the form of specially designed contact lenses. Each lens would be designed with spatially varying thickness custom made to cancel the macular distortions. Existing methods for astigmatic patients can be employed to maintain the proper orientation of each lens.

Schematic Views of Corrective Devices

Figure 7A:
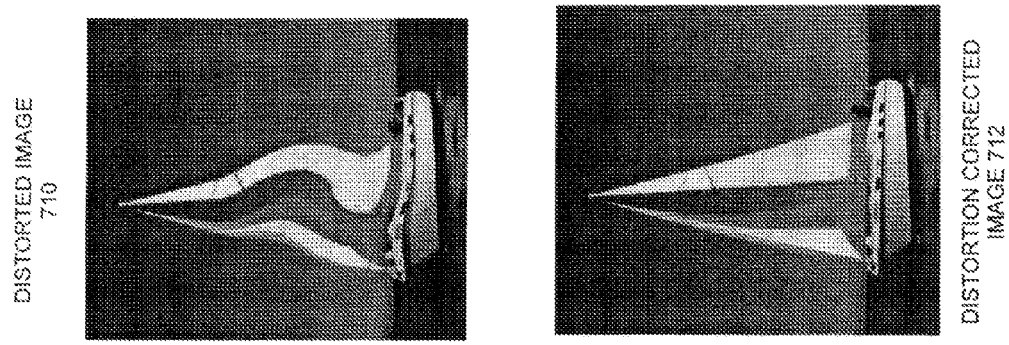
FIGS. 7A-7B illustrate an optical correction device in accordance with one or more embodiments of the present invention.
Figure 7A:
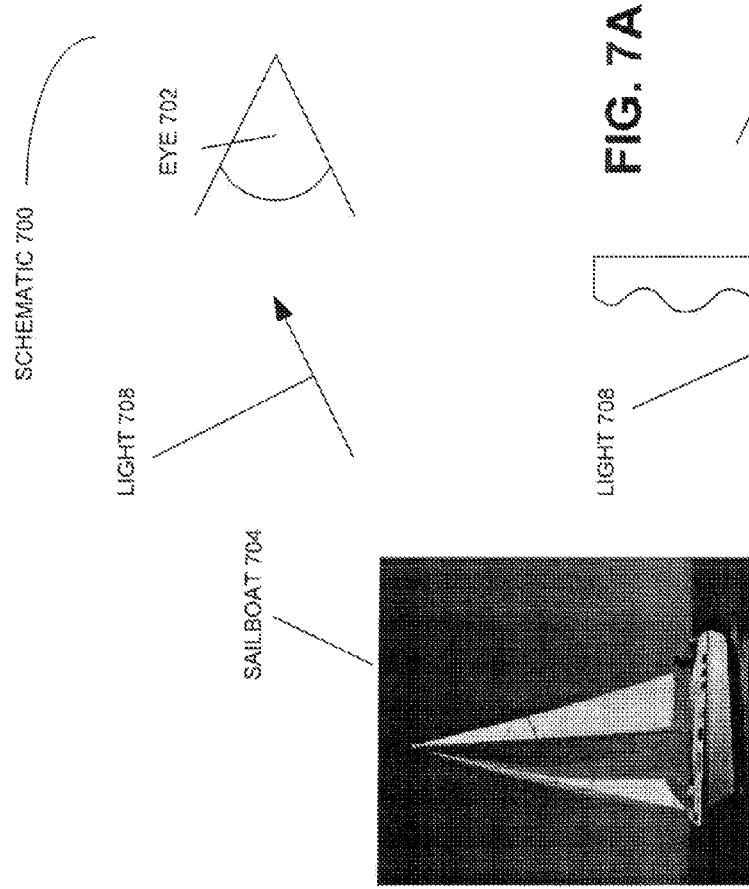
Figure 7B:
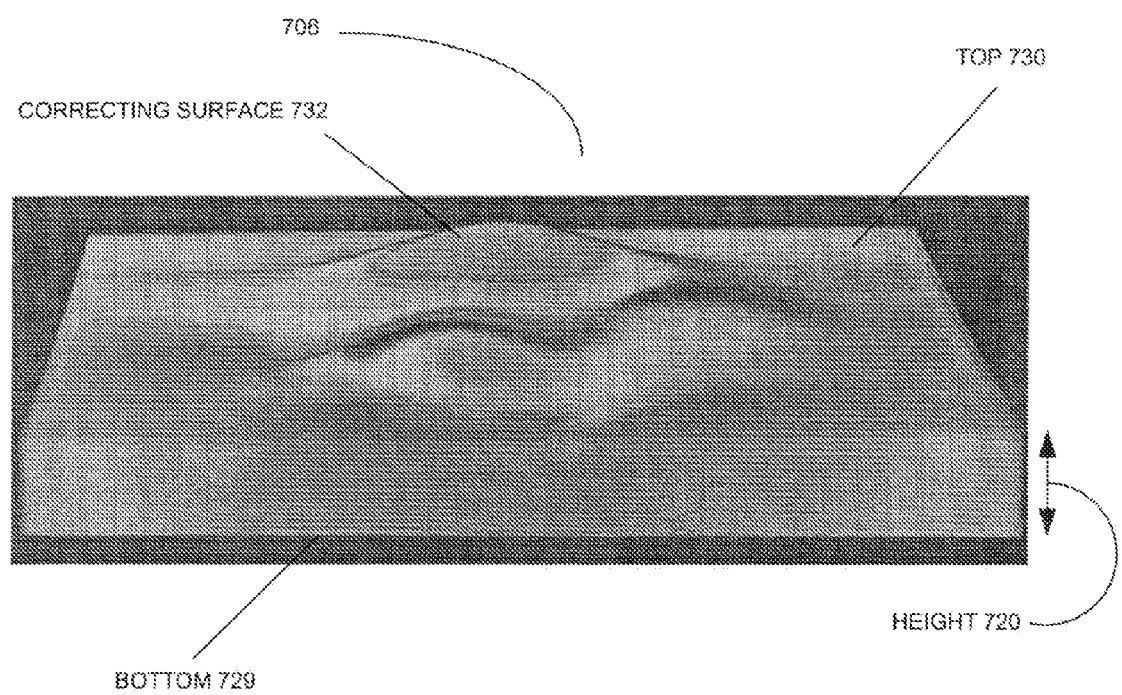

FIGS. 7A-7B illustrate an optical correction device in accordance with one or more embodiments of the present invention.

FIG. 7A illustrates schematic 700, showing eye 702 viewing sailboat 704. Device 706 is placed between eye 702 and sailboat 704, such that light 708 reflected by or emitted from sailboat 704 is viewed through device 706 by eye 702.

A person with MD looking at sailboat 704 without device 706 of the present invention would see distorted image 710. When a correcting device 706 of the present invention is interposed, the distortion is eliminated, and the person would see a distortion corrected image 712.

FIG. 7B illustrates a perspective view of a device in accordance with one or more embodiments of the present invention. FIG. 7B illustrates a slab made from glass or optical quality plastic, with dimensions such as 10×10×2 cm. The pattern on the top surface and the plate thickness are custom made so as to cancel the distortions created by the individual patient's macular degeneration.

Device 706, as shown in FIG. 7B, has been modified to include correcting surface 732, which has been determined for a given patient as described herein. To create correcting surface 732, device 706 can be machined and/or polished from top 730 down, which would reduce height 720 to a new height, or built from bottom 729 up. Although shown as a random surface, correcting surface 732 can take any shape as required by the present invention to eliminate or reduce the distortion.

Correcting surface 732 might also be formed in other ways, e.g., through the buildup of films or various materials on one or more surfaces of device 706. Various films, with different indices of refraction, or various materials, whether heterogeneous or homogeneous, can be used to create device 706 within the scope of the present invention.

Correcting surface 732 can be combined with other visual corrections, e.g., those found in typical eyeglasses, in that top 730 and/or other surfaces of device 706 can be curved or otherwise shaped to correct for astigmatism, nearsightedness, farsightedness, magnification, etc. Further, device 706 can be combined with the computer-based solution described within the scope of the present invention.

Device 706 can be employed in several embodiments within the scope of the present invention; for example, and not by way of limitation, device 706 can be used over the lens of a digital camera, such that the digital camera displays the image through device 706 to a user. Further, device 706 can be integrated into a pair of eyeglasses, which the present invention refers to as "Macular Degeneration (MD) spectacles," or used as contact lenses. Correcting surface 732 can further be placed on either or both sides of device 706, e.g., opposite top 730, such that ophthalmic devices 706 would allow for fitting to the eye or better corrective action produced by device 706.

Process Chart

Figure 8:
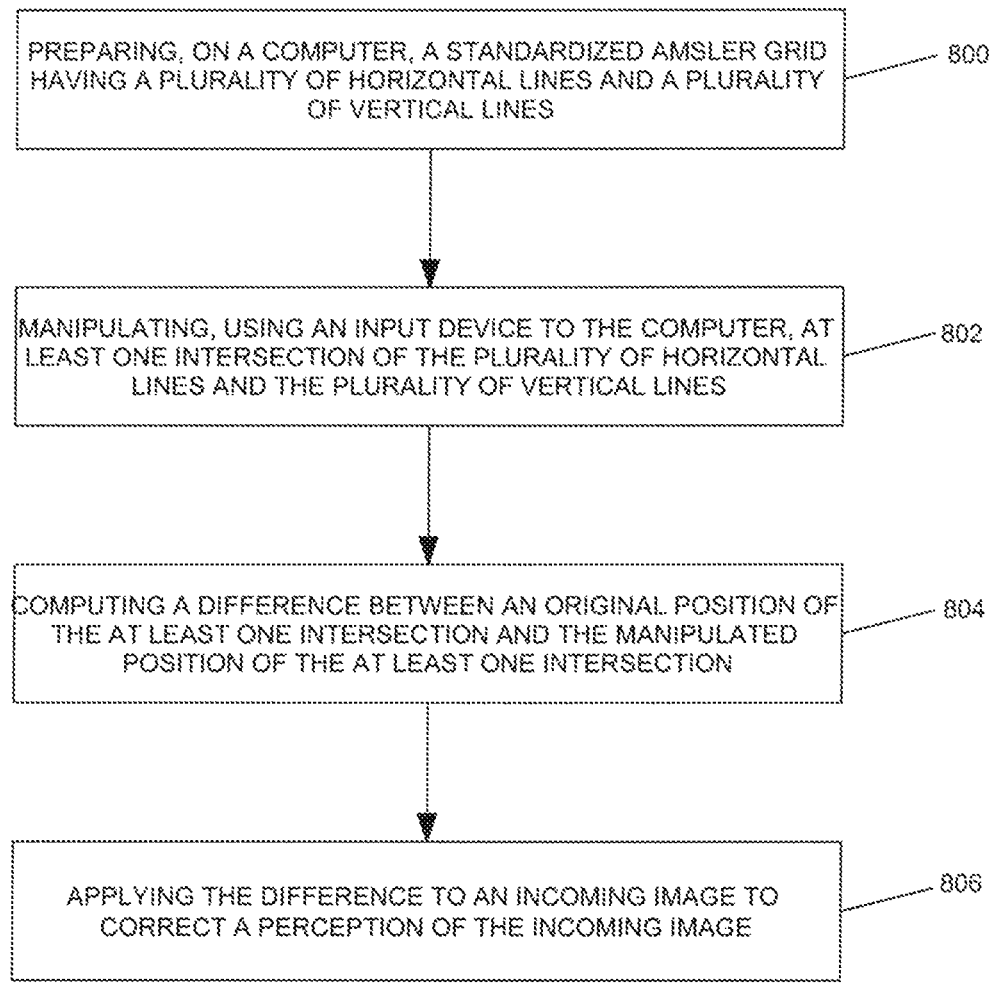
FIG. 8 illustrates a process chart in accordance with one or more embodiments of the present invention.

FIG. 8 illustrates a process chart in accordance with one or more embodiments of the present invention.

Box 800 illustrates preparing, on a computer, a standardized Amsler grid having a plurality of horizontal lines and a plurality of vertical lines.

Box 802 illustrates manipulating, using an input device to the computer, at least one intersection of the plurality of horizontal lines and the plurality of vertical lines.

Box 804 illustrates computing a difference between an original position of the at least one intersection and the manipulated position of the at least one intersection.

Box 806 illustrates applying the difference to an incoming image to correct a perception of the image.

CONCLUSION

This concludes the description of one or more preferred embodiments of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

What is claimed is:

1. A quantitative diagnostic method used to correct a patient's vision degraded by Age Related Macular Degeneration (AMD), comprising, one eye at a time:
   (A) preparing, on a computer screen, a standard Amsler Grid (AG) having a plurality of horizontal lines, a plurality of vertical lines, and a plurality of intersection points;
   (B) highlighting the center point (CP) of the standard AG;
   (C) selecting one or more of the horizontal lines and one or more of the vertical lines, and one or more of the intersection points with the selected lines;
   (D) highlighting, one at a time, these selected lines, the selected intersection points, and the boundary points of the selected lines, and designating the intersection points as original (perfect AG) intersection points;
   (E) straightening the highlighted lines according to the patient's perception, using a computer input device, while the patient's gaze is fixed on the highlighted CP, while the patient views the highlighted intersection points, and while the patient uses the highlighted boundary points as peripheral cues, to form final intersection points;
   (F) computing discrete displacement vectors between all the original (perfect AG) and corresponding final intersection points; and
   (G) applying the displacement vectors to a device to correct the patient's vision.

2. A device for quantifying a patient's vision impaired by macular degeneration, comprising:
   a computer; and
   an input device, coupled to the computer, wherein:
      the computer displays:
         a standard Amsler Grid (AG) having a plurality of horizontal lines, a plurality of vertical lines, and a plurality of intersection points and
         the center point (CP) of the standard AG, on a monitor;

the input device is configured to:

display the center point (CP) of the standard AG with a visual cue;

select one or more of the horizontal lines, one or more of the vertical lines, and one or more of the intersection points with the selected lines, wherein the intersection points are designated as original (perfect AG) intersection points, the selected intersection points, selected lines, and boundary points of the selected lines, and the CP are all displayed with visual cues on the monitor in response to the selection, and the visual cues highlight and differentiate the selected points, the selected lines, and the CP, from all non-selected points and non-selected lines; and straighten the selected line displayed with the visual cues according to the patient's perception, to form final intersection points, while the CP and the boundary points are displayed to keep the patient's eye centered, provide peripheral cues, and straighten the interior of the AG such that the lines appear straight and pass through the appropriate boundary points according to the patient's perception;

the computer computes discrete displacement vectors between all the original (perfect AG) and corresponding final intersection points; and the computer quantifies the patient's vision based on the displacement vectors.

3. The method of claim 1, further comprising:

implementing or fabricating the device for correcting the patient's vision, impaired by the AMD diagnosed using claim 1, wherein:

the device applies the displacement vectors of the AG using interpolation to any incoming image, to correct the patient's perception.

4. The method of claim 3, wherein the device is a computer device which applies the appropriate displacement vectors to the image displayed on the computer device's monitor to correct the patient's perception of the image.

5. The method of claim 4, wherein the computer device applies a dynamic compensation including:

(1) flowing reading material across an area of the computer device's screen;

(2) the computer device's screen applying the displacement vectors as a correcting distortion field to the reading material within the area; and (3) the computer device's screen displaying an indicator for adequately fixing the patient's field of view on the correcting distortion field; and wherein:

the correcting distortion field is computed using the displacement vector field obtained from claim 6 so that the patient can read the reading material.

6. The method of claim 4, further comprising:

a computer program to apply a dynamic, moving, compensating distortion field to the image, wherein the compensating distortion field is computed using interpolation of the displacement vectors; and the computer device's screen displaying and moving at least one indicator, for adequately fixing the patient's field of view on the compensating distortion; and so that the patient can read the image in real time.

7. The method of claim 3, wherein the device is a suitably patterned optical material which creates the appropriate displacement vectors to correct the patient's vision.

8. The method of claim 3, wherein the implementation further comprises a correcting optical surface, on the optical device, that simultaneously optimizes correction of the distortions caused by the AMD.

9. The method of claim 8, wherein the implementation uses Fourier mathematics.

* * * * *